United States Patent
Lee et al.

(10) Patent No.: US 7,000,382 B2
(45) Date of Patent: Feb. 21, 2006

(54) PARTIAL OXIDATION OF ALCOHOLS

(75) Inventors: Jong-Hwan Lee, Rochester Hills, MI (US); Steven J. Schmieg, Troy, MI (US); Se H. Oh, Troy, MI (US)

(73) Assignee: General Motors Corporation, Detroit, MI (US)

(*) Notice: Subject to any disclaimer, the term of this patent is extended or adjusted under 35 U.S.C. 154(b) by 146 days.

(21) Appl. No.: 10/612,661

(22) Filed: Jul. 2, 2003

(65) Prior Publication Data

US 2005/0004402 A1    Jan. 6, 2005

(51) Int. Cl.
    *F01N 3/00*      (2006.01)

(52) U.S. Cl. ............................ 60/286; 60/274; 60/301; 60/303; 423/239.1; 423/242.4; 568/471; 568/474

(58) Field of Classification Search ................. 60/274, 60/286, 295, 297, 303, 301; 423/239.1, 242.4, 423/591; 568/401, 471, 474, 479
See application file for complete search history.

(56) References Cited

U.S. PATENT DOCUMENTS

| | | | |
|---|---|---|---|
| 2,883,426 A | | 4/1959 | Brackman |
| 3,106,581 A | | 10/1963 | Neely |
| 4,471,141 A | | 9/1984 | Windawi et al. |
| 4,987,112 A | * | 1/1991 | Engler et al. ............... 502/255 |
| 5,497,617 A | * | 3/1996 | Bagley et al. ................. 60/274 |
| 5,586,433 A | | 12/1996 | Boegner et al. |
| 6,003,303 A | * | 12/1999 | Peter-Hoblyn et al. ........ 60/274 |
| 6,045,765 A | * | 4/2000 | Nakatsuji et al. ......... 423/239.1 |
| 6,176,078 B1 | | 1/2001 | Balko et al. |
| 6,314,722 B1 | * | 11/2001 | Matros et al. ................. 60/274 |
| 6,563,006 B1 | * | 5/2003 | Carter ......................... 568/449 |
| 6,787,023 B1 | * | 9/2004 | Mohr et al. ................... 208/27 |

OTHER PUBLICATIONS

Gomez, et al., Ind. Eng. Chem. Res. (1997), vol. 36, pp. 3468-3472.

* cited by examiner

*Primary Examiner*—Binh Q. Tran
(74) *Attorney, Agent, or Firm*—Kathryn A. Marra

(57) ABSTRACT

A method of partially oxidizing an alcohol to an aldehyde or ketone comprises contacting a gas containing the alcohol with a solid catalyst containing molybdenum, preferably in a +6 oxidation state, and having a surface area of 10 $m^2/g$ or higher, preferably 100 $m^2/g$ or higher. The molybdenum is supported on a high surface area carrier. The alcohol is a primary or secondary alcohol and preferably contains from 1 to 6 carbon atoms. In a preferred embodiment, the alcohol is ethanol. $NO_x$ emissions from an internal combustion engine can be lowered by combining the product of partial oxidation with the exhaust stream before passing the exhaust mixture through a lean $NO_x$ catalyst. The partial oxidation product may be generated on board and injected into the exhaust under closed loop or open loop control

27 Claims, 1 Drawing Sheet

PARTIAL OXIDATION OF ALCOHOLS

FIELD OF THE INVENTION

The invention relates to catalytic methods for the partial oxidation of alcohols to aldehydes or ketones. In particular, the invention relates to the use of the product of the catalytic partial oxidation in engine exhaust systems to reduce the level of nitrogen oxides ($NO_x$).

BACKGROUND OF THE INVENTION

Internal combustion engines, including diesel engines and spark ignition engines running on gasoline, produce small amounts of by-products in addition to the major products of combustion, carbon dioxide and water. The low level by-products include products of incomplete combustion such as carbon oxides ($CO_x$) and unburned hydrocarbons. In addition, low levels of nitrogen oxides ($NO_x$) are generally produced during combustion of fuels when oxygen partially combines with nitrogen in the air. It is generally desirable to reduce the level of these by-products to improve the quality of the environment and to achieve greater fuel efficiency as a result of more complete combustion of the fuel.

Today it is conventional to remove nitrogen oxides and incomplete combustion products from the exhaust streams of an internal combustion engine by passing the exhaust stream through a so-called three-way catalyst. The three-way catalyst catalyzes the reduction of $NO_x$ to nitrogen, the oxidation of hydrocarbons to carbon oxides ($CO_x$), and the oxidation of $CO_x$ to $CO_2$. In many commercial embodiments, the three-way catalyst is based on a combination of platinum, rhodium, and palladium. In one mode of action, the presence of hydrocarbons and carbon oxides in the exhaust stream increases the efficiency of the reduction of $NO_x$ to nitrogen by the three-way catalyst.

It is also generally desirable to increase fuel efficiency in a total combustion engine by achieving more complete combustion of the fuel. More complete combustion of the fuel increases gas mileage and lowers the emission of unburned hydrocarbons into the atmosphere. In recent years, diesel engines and lean-burn gasoline engines have been developed to increase gas mileage. Lean burn engines work by burning fuel with air in excess of that required for stoichiometric combustion of the fuel. A desirable result is that the fuel is more completely burned, thereby increasing fuel economy.

Because of the higher efficiency of combustion of the fuel, the level of unburned hydrocarbons is reduced in the exhaust stream of diesel engines and gasoline engines running under lean burn conditions. As a result, the conventional three-way catalysts are less efficient at reducing nitrogen oxides, because there is less hydrocarbon and carbon oxide in the exhaust stream to aid in that reduction.

It would therefore be desirable to provide methods for enhancing the reduction of nitrogen oxides to nitrogen in a catalytic system, especially in engines with a reduced level of unburned hydrocarbons in the exhaust.

SUMMARY OF THE INVENTION

The present invention provides methods for lowering the level of nitrogen oxides in the emissions of an internal combustion engine by passing exhaust gas generated by the engine over a reducing catalyst. Before passing over the reducing catalyst, the exhaust gas is combined with a reducing gas that increases the efficiency of the reduction of nitrogen oxides to nitrogen. The reducing gas is produced onboard a motor vehicle by passing a gas composition containing an alcohol over an oxidizing catalyst. The oxidizing catalyst catalyzes the partial oxidation of the alcohol to an aldehyde or a ketone.

In a preferred embodiment, acetaldehyde is generated onboard during operation of the vehicle by the partial oxidation of ethanol to acetaldehyde. Other products of partial oxidation of alcohols may also be used.

In another embodiment, methods are provided for the controlled partial oxidation of alcohols to ketones or, preferably, aldehydes. Carboxylic acids may also be produced. In one embodiment, the production of carboxylic acids and higher oxidation products is minimized to increase the yield of aldehyde or ketone. In a preferred embodiment, yields of 70% or greater of aldehyde can be achieved, along with near complete conversion of the alcohol. By the methods of the invention, primary and secondary alcohols containing 1 to 6 carbons may be oxidized to the corresponding aldehyde or ketone. In a preferred embodiment, ethanol is converted to acetaldehyde at a yield of 70% or greater.

Motor vehicles and their emission control systems include, in addition to the conventional engine, exhaust gas path, and reducing catalyst, a source of alcohol, preferably ethanol, and an oxidizing catalyst disposed such that alcohol enters the inlet of the oxidizing catalyst, while the product of partial oxidation of the alcohol leaves the outlet of the oxidizing catalyst and is directed to the exhaust path of the engine, where it enters the path upstream of the reducing catalyst.

The methods and emission control systems of the invention all make use of an oxidizing catalyst containing molybdenum, preferably as a $Mo^{+6}$ atomic species. In one aspect, the catalyst contains $MoO_3$ on a carrier that provides the catalyst with a surface area sufficiently large to catalyze the partial oxidation at an acceptable rate. In a preferred embodiment, the surface area of the catalyst is 10 $m^2/g$ or greater, preferably 50 $m^2/g$ or greater, and more preferably 100 $m^2/g$ or greater.

The catalyst may be prepared by calcining a molybdenum compound in the presence of a carrier having a high surface area. Suitable carriers include insoluble oxides of elements having only one common oxidation state such as, without limitation, zeolites, alumina, silica, titania, zirconia, and magnesia. Preferred carriers are less-acidic or non-acidic. Alumina, and especially γ-alumina and activated aluminas based on γ-alumina are particularly preferred. Typically the catalyst contains 1 to 30% molybdenum by weight, preferably 1 to 20%, and operates to convert alcohols to aldehydes and ketones at temperatures of about 200–300° C. with yields as high as 90%.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
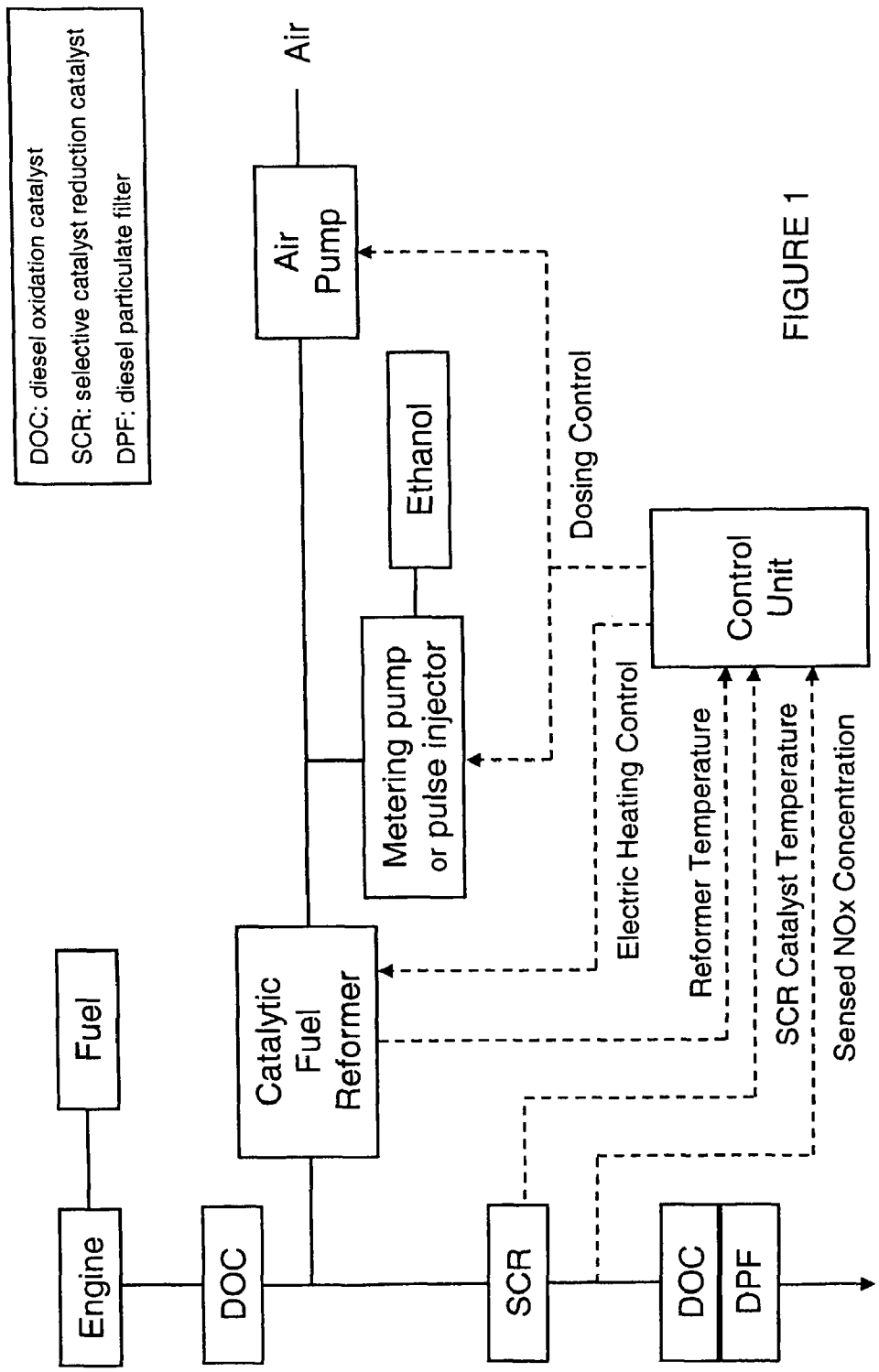
FIG. 1 is a block schematic diagram of a emission control system incorporating the oxidizing catalyst of the invention.

The following description of the preferred embodiment(s) is merely exemplary in nature and is in no way intended to limit the invention, its application, or uses.

In one embodiment, a method of partially oxidizing an alcohol to an aldehyde or ketone comprises contacting a gas containing the alcohol with a solid catalyst composition. The solid catalyst compositions contain molybdenum, preferably in a +6 oxidation state, and have a surface area of 10 m$^2$/g or higher, preferably 100 m$^2$/g or higher. In some embodiments, the molybdenum is present as $MoO_3$, and is supported on a carrier selected from water insoluble oxides such as alumina, titania, silica and zirconia. The catalyst generally contains from about 1 to about 30% by weight molybdenum, preferably from about 1 to 20% by weight molybdenum. The alcohol is a primary or secondary alcohol and preferably contains from 1 to 6 carbon atoms. In a preferred embodiment, the alcohol is ethanol.

In another embodiment, a method for oxidizing ethanol to acetaldehyde is provided, that comprises contacting a gas comprising ethanol with the solid state catalyst as described above. Preferably, the solid state catalyst contains molybdenum supported on a carrier selected from the group consisting of silica, titania, alumina and zirconia. In some embodiments, the gas comprises 10% or greater by volume oxygen. In other embodiments, the gas comprises air. In a preferred embodiment, the amount of ethanol in the gas is about 1.5% by volume or less.

In further embodiments, methods for lowering $NO_x$ emissions from an internal combustion engine are provided. Exhaust gas generated from the internal combustion engine is passed over a reducing catalyst. Prior to passing over the reducing catalyst, the exhaust gas is combined with a reducing gas generated by passing an alcohol over an oxidation catalyst as described above. The oxidizing catalyst catalyzes the partial oxidation of the alcohol to an aldehyde or ketone, preferably at yields of 50% or greater.

In a particularly preferred embodiment, a method for lowering $NO_x$ emissions in the exhaust stream of an internal combustion engine in an operating motor vehicle is provided, whereby acetaldehyde is combined with the exhaust stream upstream of a selective reduction catalyst. The acetaldehyde combined with the exhaust stream increases the efficiency of the selective reduction catalyst, which can be a conventional three-way automotive catalyst or, preferably, a lean $NO_x$ catalyst based on, for example, alumina or zeolite. In a particularly preferred embodiment, the acetaldehyde is generated onboard the motor vehicle by passing gaseous ethanol over an oxidizing catalyst as described above.

In still further embodiments, the invention encompasses a control system for reducing nitrogen oxide concentration in the exhaust stream of an internal combustion engine. The control system includes, in addition to standard internal combustion engine, catalytic converter and an exhaust path connecting the engine and converter, a source of ethanol and an oxidizing catalyst assembly. The oxidizing catalyst assembly has an inlet connected to the ethanol source and an outlet connected to the exhaust path upstream of the catalytic converter. The catalytic converter holds a selective catalyst reduction catalyst and the oxidizing catalyst assembly contains an oxidizing catalyst such as described above.

The oxidizing catalyst for use in the invention contains molybdenum on a carrier having a sufficiently high surface area to efficiently convert the alcohol to an aldehyde or a ketone. The oxidizing catalyst generally contains from about 1 to 30% by weight molybdenum, preferably 1 to 20% by weight. In preferred embodiments, the catalyst contains about 5 to 15% by weight molybdenum, wherein the level of molybdenum is chosen to balance the cost and efficiency of the catalyst. As a general rule, it is desirable to provide catalyst having molybdenum levels sufficiently high to convert, preferably completely, the alcohol to reaction products including aldehydes and ketones, while also minimizing the costs of the catalyst by limiting the amount of molybdenum.

In one embodiment, the active ingredient of the oxidizing catalyst is molybdenum trioxide, which is finely distributed on a carrier having a high surface area. In a preferred embodiment, the surface area of the carrier is greater than or equal to 10 m$^2$/g, preferably greater than or equal to 50 m$^2$/g and more preferably greater than or equal to 100 m$^2$/g.

Carriers for the molybdenum catalysts of the invention generally comprise insoluble oxides or mixed oxides of elements that either exist in only one oxidation state, or that are otherwise comparatively inactive in the partial oxidation of alcohols in that they do not lead to an unacceptable level of by-product that would reduce the yield of aldehyde or ketone below a desired level. Such elements include Al, Ti, Zr, Si, Ga, Ge, and In. The carriers may be mixed oxides of the above with elements such as Mg, Ca, Na, and K, as long as the carriers remain sufficiently water-insoluble. Exemplary carriers include alumina, silica, titania, and zirconia. Mixed oxides include the zeolites, which are generally mixed Al and Si oxides, with optional cations such as Mg, Ca, Na, and K. The acidity of these solid materials depends on the composition, phase, and level of defects. For example, the acidity of zeolites depends in part on the ratio of Al to Si. Titania exists in a more acidic phase (rutile) and in a slightly acidic or neutral phase (anatase).

To the extent that the surface acidity of oxide carriers would tend to lead to production of undesired by-products, it is preferred to use less-acidic or non-acidic carriers. As a general rule, such carriers are commercially available having surface areas in the desired range. Thus, alumina is readily commercially available having typical values of surface areas in ranges from 100 to 200 m$^2$/g. A preferred commercial grade is γ-alumina. In addition, silica is available commercially having surface areas of 100 to 200 and even up to 300 m$^2$/g. Additionally, titania is commercially available having surface areas from 50 to 200 m$^2$/g.

The oxidizing catalyst of the invention may be prepared by calcining a molybdenum compound in the presence of the carrier. In general, the oxidizing catalyst is prepared by conventional methods of syntheses, which are known by such terms as incipient wetness method, wet impregnation methods, and ion exchange methods. To illustrate, in the incipient wetness method, a molybdenum solution is first prepared by dissolving a molybdenum precursor such as ammonium molybdate in water, such that the volume of the solution matches the pore volume of a support material. The resulting solution is then added to a support material such as alumina, silica, titania or zirconia. The resulting product is dried, for example, overnight at 110° C. to drive off excess water. Thereafter, the product may be calcined, for example at 450° C. for four hours. An oxide of molybdenum such as $MoO_3$ is produced during the calcining step, and is believed to be an active component of the catalyst.

The wet impregnation method is similar to the incipient wetness method except that the volume of the molybdenum solution is not limited to that which fills the pore volume of the support material. In the wet impregnation method, an amount of carrier is combined with a molybdenum solution that has a volume greater than the pore volume. The excess water is allowed to evaporate, after which the product is calcined as before. Use of the wet impregnation process to make the catalyst of the invention may lead to the ability to incorporate higher levels of molybdenum than the incipient wetness method.

In the ion exchange method, a solution of molybdenum precursor is contacted with an amount of carrier. The carrier and precursor combination may be shaken or stirred for a period of time to enable molybdenum ions to exchange with protons on the surface of the carrier. Thereafter, the solids may be filtered out and calcined as before. As a general rule, the ion exchange method is used to incorporate relatively lower amounts of molybdenum onto the non-acidic carrier. In effect, the amount of molybdenum incorporation is limited by the number of anchoring spots on the carrier.

The partial oxidation reactions of the alcohol are normally carried out in the vapor phase. A gaseous alcohol, or preferably a mixture of gases containing the alcohol, is passed through the catalyst at a rate chosen to give the desired conversion and yield at the operating temperature, taking into account the surface area of the catalyst. In a preferred embodiment, the mixture of gases including the alcohol contains air and water vapor. Water vapor may originate from water in the alcohol source or from the moisture in ambient air.

Advantageously, the catalysts of the invention are effective at converting alcohol to aldehyde or ketone even in relatively oxidizing conditions, such as gases containing 10% or greater by oxygen, or air which contains about 19% oxygen. Conversions of 80% or greater and preferably 90% or higher may be readily achieved. In preferred embodiments, essentially complete conversion of alcohol is achieved. Yield of partial oxidation product is preferably 50% or greater, and preferably 70% or greater. Acceptable conversions of alcohol and yield of partial oxidation products may be obtained at temperatures of 150–350° C., preferably 175–325° C., and more preferably 200–300° C., with molybdenum loadings of 1 to 30% by weight, preferably 1–20% by weight.

In a preferred embodiment, the alcohol makes up a minor amount by weight or volume of the gas containing the alcohol. In a preferred embodiment, the alcohol is less than 10% by volume, more preferably less than 5% by volume, and even more preferably less than 1.5% by volume of the gas mixture passed through the catalyst. The amount of alcohol that can be oxidized generally depends on the duration of contact of the alcohol with the catalyst and the amount of catalyst relative to alcohol. If higher conversion is required, the reaction time may be increased by, for example, increasing the reaction path of a tubular reaction through which the alcohol passes.

Alcohols that may be partially oxidized according to the invention include organic alcohols that can be put into the vapor or gaseous state at the temperatures of reaction. In a preferred embodiment, the alcohols for partial oxidation by the invention are selected from those having one to eight carbon atoms, preferably 1 to 6 carbon atoms. The alcohols are either primary alcohols or secondary alcohols. The primary alcohols are partially oxidized to an aldehyde, while the secondary alcohols are partially oxidized to ketones. Non-limiting examples of preferred alcohols include methanol, ethanol, propanol, isopropanol, n-butanol, 2-butanol, 1-pentanol, and 1-hexanol. Thus, methanol may be partially oxidized to formaldehyde, ethanol to acetaldehyde, propanol to propionaldehyde, isopropanol to acetone, n-butanol to butyraldehyde, 2-butanol to methyl ethyl ketone, and so on.

In some embodiments for use in motor vehicles, ethanol is a preferred alcohol. The acetaldehyde produced by partial oxidation of ethanol is a preferred reactive reducing gas for improving the efficiency of $NO_x$ reduction by conventional three-way catalysts. Accordingly, the invention will be further described below in a non-limiting way with respect to the ethanol and acetaldehyde. It is to be understood the invention is not limited thereby, but that other alcohol/partial oxidation products may be used in the invention.

The invention also encompasses a control system for $NO_x$ reduction incorporating a catalyst according to the invention. The control system contains an internal combustion engine, a catalytic converter, and a connecting pipe between the engine and the converter that provides an exhaust path and defines a downstream direction away from the engine toward the catalytic converter. In this embodiment, the invention includes a source of ethanol disposed within the vehicle emission system in such a way as to deliver a gas stream containing ethanol vapor (preferably less than 1.5% in air) into the inlet of an oxidizing catalyst, where it undergoes catalytic conversion to acetaldehyde. The source of ethanol may be derived from a fuel tank containing an ethanol fuel. In another embodiment, for example when the fuel contains less than 100% ethanol, ethanol may be separated from the fuel by distillation, with the ethanol fraction directed to the oxidizing catalyst. In another embodiment, the source of ethanol may be held in the vehicle in a secondary tank. The tank may be conveniently filled by the consumer as required. Optionally, upon filling the fuel tank, with engine fuel containing an amount of ethanol (for example 1.5% ethanol), ethanol can be obtained from the rest of the fuel immediately by distillation and stored in a separate tank.

FIG. 1 illustrates an embodiment of an engine emission control system utilizing the oxidizing catalyst of the invention. FIG. 1 illustrates a particular embodiment for a diesel engine including diesel oxidation catalyst that function to remove carbon monoxide, hydrocarbons, aldehydes, and diesel particulate matter from the exhaust stream. As shown in FIG. 1, ethanol is delivered into a catalytic fuel reformer containing an oxidizing catalyst according to the invention. Ethanol may be delivered, in non-limiting examples by a metering pump or by a pulse injector. At the same time an air pump operates to blend air with ethanol for input into the catalytic fuel reformer. As shown, the output of the catalytic fuel reformer, which contains the partial oxidation product of the ethanol, is combined into the engine exhaust stream upstream of the SCR catalyst (selective catalyst reduction catalyst) where NOx is reduced to nitrogen. In the embodiment of FIG. 1, the exhaust stream proceeds through a second diesel oxidation catalyst, through a diesel particulate filter, and out the exhaust system into the atmosphere.

The system may take advantage of conventional control processes for achieving an optimum level of nitrogen oxides and other components in the exhaust stream. For example as shown, a control unit receives input from the catalytic fuel reformer, the SCR catalyst, and a nitrogen oxide sensor downstream of the SCR catalyst. Using inputs such as the reformer temperature, the catalyst temperature, and a sensed $NO_x$ concentration, the control unit may be programmed to provide dosing control to the metering pump and air pump that determines the amount of ethanol and air respectively provided to the inlet of the catalytic fuel reformer. In addition, the control unit may control the electric heating of the oxidizing catalyst in the catalytic fuel reformer.

Open loop control systems may also be used. Open loop control systems utilize engine parameters such as engine rpm, temperature, load, and the like. When utilizing open loop control, it is conventional to determine a so-called "engine map" of the response of emissions to emission system variables as a function of engine conditions by empirical methods. Such methods are well known in the art and may be adapted to provide emission control in the systems of the invention.

The catalytic fuel reformer containing the oxidizing catalyst may be provided in the form of a monolith surrounded by insulation and an insulation cover. As is conventional in the field, the monolith may be made of ceramic, and provide a plurality of honey comb surfaces through which a gas-containing vaporous alcohol may be drawn to contact the oxidizing catalyst held on the substrate members of the monolith. The monolith may be made of a ceramic material such as cordierite. In another embodiment, the monolith may be provided as a metallic monolith, such as the structured metal foils provided by Emitech GmbH. The metallic monolith are more expensive, but they are better suited when it is desired to heat the oxidizing catalyst during operation of the emission reduction system.

The description of the invention is merely exemplary in nature and, thus, variations that do not depart from the gist of the invention are intended to be within the scope of the invention. Such variations are not to be regarded as a departure from the spirit and scope of the invention.

EXAMPLES

Example 1

Preparation of Catalyst

A catalyst with a 10% loading of Mo was prepared in the following way. First, 0.49 grams of ammonium heptamolybdate tetrahydrate, $(NH_4)_6Mo_7O_{24} \cdot 4H_2O$) was dissolved in 1.7 ml of water. The Mo solution was then added to 2.5 grams of γ-alumina. The resulting wet solid was warmed under an IR lamp for drying excess water for 1–2 hours, and then further dried in a drying oven at 110° C. overnight. The catalyst was then heated at 5° C./min and calcined at 450° C. for 4 hours. The resulting catalyst was always pressed and sieved before use, and only the 60–80 mesh-sized particles were tested for the reaction. Different weight loadings (1, 3, 5, 7, 10, 15 and 20%) were prepared by dissolving correspondingly more or less Mo precursor in the same 1.7 ml of water. The wet impregnation method may also be used, especially where higher loadings of Mo are required.

Example 2

0.23 grams of a catalyst as prepared in Example 1, having molybdenum loadings of 1 to 20%, are placed in a ¼ inch quartz tube reactor. The quartz tube is heated in an electrically heated furnace to the temperatures given in tables 1 and 2. A mixture of gas containing 19% oxygen, 2.5% water, and about 0.1% ethanol was flowed through the quartz tube reactor. The products were monitored with Fourier transform infrared spectroscopy (FTIR). A flow rate was chosen so as not to be limiting as to ethanol conversion or yield of acetaldehyde. It was found that the catalytic partial oxidation could be carried out at a wide range of flow rates.

The mixture of gases was prepared by using a syringe pump to inject ethanol to a wick. In the same manner, a second wick was saturated with water. An air stream was blown across the wick containing ethanol and the wick containing water to provide the input gas to the quartz tube reactor. The total flow rate was 272 ml/min. The ethanol concentration in the input gas was about 1160 ppm by volume. The water concentration in the input gas was about 2.5% by volume.

Catalysts containing molybdenum loadings of 1, 3, 5, 7, 10, 15 and 20% were used to catalyze the partial oxidation of ethanol at temperatures of 175, 200, 225, 250, 275, 300 and 325° C. Ethanol conversion is defined as ethanol in minus ethanol out, the difference being divided by the amount of ethanol in, the dividend being multiplied by 100 to provide the percent ethanol conversion. The ethanol out was determined by FTIR as discussed above. The acetaldehyde yield is defined by the amount of acetaldehyde out, as determined by FTIR, divided by the amount of ethanol in, the dividend being multiplied by 100 to give the percent acetaldehyde yield.

Tables 1 and 2 show the results of experiments at the different temperatures mentioned above. Table 1 shows the effect of molybdenum loading in the catalyst on the conversion of ethanol at different temperatures, while Table 2 shows the effect of molybdenum loading on acetaldehyde yield.

TABLE 1

Ethanol conversion as a function of Mo loading and temperature.

| | | Temperature ° C. | | | | | |
|---|---|---|---|---|---|---|---|
| | | 175 | 200 | 225 | 250 | 275 | 300 | 325 |
| % Mo by weight in catalyst | 1 | | | | 51 | 72 | 88 | 94 |
| | 3 | | | 54 | 85 | 93 | 98 | |
| | 5 | | 60 | 93 | 99 | 100 | 100 | |
| | 7 | | | 95 | 100 | 100 | 100 | |
| | 10 | 40 | 90 | 100 | 100 | 100 | | |
| | 15 | 60 | 97 | 100 | 100 | 100 | | |
| | 20 | 63 | 96 | 100 | 100 | 100 | | |

TABLE 2

Yield of acetaldehyde as a function of Mo loading and temperature.

| | | Temperature ° C. | | | | | |
|---|---|---|---|---|---|---|---|
| | | 175 | 200 | 225 | 250 | 275 | 300 | 325 |
| % Mo by weight in catalyst | 1 | | | | 41 | 55 | 55 | 39 |
| | 3 | | | 41 | 69 | 71 | 68 | |
| | 5 | | 53 | 76 | 77 | 75 | 71 | |
| | 7 | | | 84 | 79 | 77 | 75 | |
| | 10 | 41 | 75 | 89 | 75 | 72 | | |
| | 15 | 51 | 80 | 84 | 77 | 72 | | |
| | 20 | 52 | 77 | 79 | 76 | 69 | | |

What is claimed is:

1. A method of lowering $NO_x$ emissions from an internal combustion engine by passing exhaust gas generated by the combustion of fuel in the engine over a reducing catalyst, the method comprising passing a gas composition comprising an alcohol over an oxidizing catalyst to produce a reducing gas; and combining the reducing gas with the exhaust gas upstream of the reducing catalyst, wherein the oxidizing catalyst catalyzes the partial oxidation of the alcohol to an aldehyde or ketone.

2. A method according to claim 1, wherein the oxidizing catalyst comprises molybdenum in a +6 oxidation state and has a surface area greater than or equal to 10 $m^2/g$.

3. A method according to claim 2, wherein the surface area is greater than or equal to 50 $m^2/g$.

4. A method according to claim 2, wherein the surface area is greater than or equal to 100 m²/g.

5. A method according to claim 1, wherein the oxidizing catalyst comprises molybdenum supported on a carrier selected from the group consisting of alumina, silicia, titania, and zirconia.

6. A method according to claim 1, wherein the alcohol comprises ethanol.

7. A method according to claim 1, wherein the oxidizing catalyst comprises molybdenum supported on alumina.

8. A method according to claim 5, wherein the oxidizing catalyst comprises 1 to 20% by weight molybdenum.

9. A method according to claim 1, further comprising detecting a level of $NO_x$ in the exhaust stream and controlling the rate of combining the reducing gas with the exhaust gas based on the level of $NO_x$.

10. A method for lowering $NO_x$ emissions in the exhaust stream of an internal combustion engine in an operating motor vehicle by combining acetaldehyde with the exhaust stream upstream of a selective reduction catalyst, comprising: generating the acetaldehyde onboard the motor vehicle by passing a gas comprising ethanol over an oxidizing catalyst to produce the acetaldehyde, wherein the oxidizing catalyst comprises molybdenum supported on a carrier selected from the group consisting of alumina, silica, titania and zirconia.

11. A method according to claim 10, wherein the carrier comprises alumina.

12. A method according to claim 11, wherein the oxidizing catalyst comprises 1 to 20% by weight molybdenum.

13. A method according to claim 10, wherein the acetaldehyde is produced at a yield of greater than or equal to 50% from the ethanol.

14. A method according to claim 13, wherein the yield is greater than or equal to 70%.

15. A method according to claim 10, wherein the gas comprises greater than 10% by volume oxygen.

16. A method according to claim 10, wherein the gas comprises air.

17. A method according to claim 10, wherein the gas comprises less than or equal to 1.5% by weight ethanol.

18. A control system for $NO_x$ reduction, comprising:
an internal combustion engine;
a catalytic converter;
a connecting pipe between the engine and catalytic converter providing an exhaust path and defining a downstream direction away from the engine toward the catalytic converter;
a source of ethanol; and
an oxidizing catalyst assembly having an inlet connected to the ethanol source and an outlet connected to the exhaust path upstream of the catalytic converter,
wherein the catalytic converter holds a selective catalyst reduction catalyst, and the oxidizing catalyst assembly contains an oxidizing catalyst that catalyzes the partial oxidation of ethanol to acetaldehyde at a yield of 50% or greater.

19. A control system according to claim 18, wherein the source of ethanol is engine fuel carried in a fuel tank connected to the engine.

20. A control system according to claim 18, wherein the source of ethanol is a secondary tank.

21. A control system according to claim 18, wherein the oxidizing catalyst comprises $Mo^{+6}$ and has a surface area greater than or equal to 10 m²/g.

22. A control system according to claim 21, wherein the surface area is greater than or equal to 50 m²/g.

23. A control system according to claim 21, wherein the surface area is greater than or equal to 100 m²/g.

24. A control system according to claim 18, wherein the oxidizing catalyst comprises molybdenum supported on a carrier selected from the group consisting of alumina, silica, titania and zirconia.

25. A control system according to claim 24, wherein the carrier comprises alumina.

26. A control system according to claim 24, wherein the oxidizing catalyst comprises 1 to 20% by weight molybdenum.

27. A control system according to claim 25, wherein the oxidizing catalyst comprises 1 to 20% by weight molybdenum.

* * * * *